United States Patent
Mishra et al.

(10) Patent No.: US 7,937,225 B2
(45) Date of Patent: May 3, 2011

(54) SYSTEMS, METHODS AND SOFTWARE ARRANGEMENTS FOR DETECTION OF GENOME COPY NUMBER VARIATION

(75) Inventors: Bhubaneswar Mishra, Great Neck, NY (US); Archisman Rudra, Bronx, NY (US); Raoul-Sam Daruwala, Jersey City, NJ (US)

(73) Assignee: New York University, New York, NY (US)

( * ) Notice: Subject to any disclaimer, the term of this patent is extended or adjusted under 35 U.S.C. 154(b) by 1478 days.

(21) Appl. No.: 11/212,219

(22) Filed: Aug. 25, 2005

(65) Prior Publication Data

US 2006/0078917 A1 Apr. 13, 2006

Related U.S. Application Data

(60) Provisional application No. 60/607,321, filed on Sep. 3, 2004.

(51) Int. Cl.
 *G01N 33/48* (2006.01)
(52) U.S. Cl. ........................................................ 702/19
(58) Field of Classification Search .................. 702/19
 See application file for complete search history.

(56) References Cited

OTHER PUBLICATIONS

Albertson, Donna et al., "Genomic microarrays in human genetic disease and cancer.", *Human Molecualar Genetics*, vol. 12, Review Issue 2, DO1:10.1093/hmg/ddg261 Cancer Research Institute and Department of Laboratory Medicine, 2003 , R145-R152.
Berger, James O. et al., "On the Development of Reference Priors", *Bayesian Statistics 4, Oxford University Press, 1992* 1992 , 35-60.
Bernardo, Jose et al., "Reference Posterior Distributions for Bayesian Inference", *Journal of the Royal Statistical Society. Series B (Methodological)*, vol. 41, No. 2 1979 , 113-147.
Brown, L. D. , "Admissible Estimators, Recurrent Diffusions, and Insoluble Boundary Value Problems", *The annals of Mathematical Statistus*, vol. 42, No. 3. Jun. 1971 , 855-903.
Brown, Lawrence D. , "An Essay on Statistical Decision Theory", *American Statistical Association*, vol. 95, No. 452 Dec. 2000 , 1277-1281.
Jeffreys, Harold et al., "An Invariant Form for the Prior Probability in Estimation Problems.", *Proceedings of the Royal Society of London. Series A. Mathematical and Physical Sciences*, vol. 186, No. 1007 Sep. 24, 1946 , 453-461.
Kass, Robert E. et al., "The Selection of Prior Distributions by Formal Rules", *Journal of the American Statistical Association*, vol. 91, No. 435 9 1996 , 1343-1370.
Lisitsyn, Nikolai et al., "Cloning the Differences Between Two Complex Genomes", *Science*, vol. 259 Feb. 12, 1993 , 946-951.
Lucito, Robert et al., "Detecting Gene Copy Number Fluctuations in Tumor Cells by Microarray Analysis of Genomic Representations", *Genome Research* vol. 10 2000 , 1726-1736.
Lucito, Robert et al., "Genetic Analysis Using Genomic Representations", *Proc. Natl. Acad. Sci. USA*, vol. 95, Apr. 1998 , 4487-4492.
Mishra, Bud , "Comparing Genomes", *Computing in Science & Engineering*, IEEE, 2002 , 1521-9615.
Strawderman, William E. , "Minimax Estimation of Location Parameters for Certain Spherically Symmetric Distributions", *Journal of Multivariate Analysis 4* 1974 , 255-264.
Strawderman, William E. et al., "Minimaxity", *Journal of the American Statistical Association*, vol. 95, No. 452 Dec. 2000 , 1364-1368.
Strawderman, William E. , "Proper Bayes Minimax Estimators of the Multivariate Normal Mean", *The Annals of Mathematical Statistics*, vol. 42, No. 1. 1971 , 385-388.
Berger, 1985, *Statistical Decision Theory and Bayesian Analysis*, $2^{nd}$ edition. Springer-Verlag, New York.
Anderson, 1958, *An Introduction to Multivariate Statistical Analysis*, Wiley, New York.
Wilks, 1962, *Mathematical Statistics*. Wiley, New York.
Raiffa & Schlaifer, 1961, *Applied Statistical Decision Theory*. Division of Research, Graduate School of Business Administration, Harvard University.
Bernardo and Smith (*Bayesian Theory*. Wiley , New York, 1994).
Berger (*Statistical Decision Theory and Bayesian Analysis*. 2nd edition, Springer-Verlag, New York, 1985).
Carlin et al. (*Bayes and Empirical Bayes Methods for Data Analysis*. Chapman & Hall, London, 1996).
Gelman et al. (*Bayesian Data Analysis*. Chapman & Hall, London, 1995).
Robert (*The Bayesian Choice*. Springer, New York, 2001).
Brown, 1993, *In Statistical Decision Theory and Related Topics 5, Gupta and Berger (eds)*, Springer-Verlag, New York, pp. 1-18.
Brown, 1986, IMS Lecture Notes, Monograph Series 6. Hayward, Calif.

*Primary Examiner* — Jerry Lin
(74) *Attorney, Agent, or Firm* — Dorsey & Whitney LLP

(57) ABSTRACT

The present invention relates to systems, methods and software arrangements for the detection of variations in the copy number of a gene in a genome. These systems, methods and software arrangements are based on a simple prior model that uses a first process generating amplifications and deletions in the genome, and a second process modifying the signal obtained to account for the corrupting noise inherent in the technical methodology used to scan the genome. A Bayesian approach according to the present invention determines, e.g., the most plausible hypothesis of regional changes in the genome and their associated copy number. The systems, methods, and software arrangements can be are framed as optimization problems, in which a score function is minimized. The system, methods and software arrangements may be useful to assist the scientific study, diagnosis and/or treatment of any disease which has a genetic component, including but not limited to cancers and inherited diseases.

43 Claims, 7 Drawing Sheets

US 7,937,225 B2

SYSTEMS, METHODS AND SOFTWARE ARRANGEMENTS FOR DETECTION OF GENOME COPY NUMBER VARIATION

CROSS-REFERENCE TO RELATED APPLICATION

The present application claims priority from U.S. Provisional Patent Application No. 60/607,321, filed Sep. 3, 2004, entitled "Systems, Methods and Software Arrangements for Detection of Genome Copy Number Variation," the disclosure of which is incorporated herein by reference in its entirety.

FIELD OF THE INVENTION

The present invention relates to systems, methods and software arrangements for determination of variations in the copy number of a gene in a genome. This invention can use a model that analyzes genomic amplification or deletion processes in terms of parameters that may be dependent only upon the number of segments affected ($p_b$) and the segment sizes ($p_r$), and can be resistant to the technology-dependent additive noise that may be present in the dataset. The system, method, and software arrangement according to the present invention may be useful to assist in the scientific study, diagnosis, and/or treatment of any disease which has a genetic component, including but not limited to cancers and inherited diseases.

BACKGROUND INFORMATION

Genomes in a population are polymorphic, giving rise to diversity and variation. In cancer, even somatic cell genomes can rearrange themselves, often resulting in parts of the genome getting deleted (hemi- or homozygously), causing a decrease in copy number of a gene, or getting amplified, causing an increase in copy number of a gene. The ability to study these chromosomal aberrations quickly, inexpensively and accurately has important and useful scientific, clinical and therapeutic implications, particularly, in the genomics of cancer and inherited diseases. See Lucito et al., 2000, *Genome Research* 10:1726-1736; Mishra, 2002, *Computing in Science and Engineering* 4:42-49. Cancer genome-based methods, in contrast to gene expression-based methods, are able to take advantage of the fact that DNA is a stable component of a cancer cell that does not vary as a function of the cell's physiological state. Even though they may be crude, karyotyping, determination of ploidy, and comparative genomic hybridization provide an arsenal of useful biotechnological tools for this purpose, and produce data that demand treatment by sophisticated statistical algorithms to be reliable clinical guides for diagnosis and treatment.

Microarray methods appear to be the most dominant of the new technologies used to study variations between normal and cancer genomes. One can sample the genome uniformly (independent identically distributed) and reproducibly to create a large number of oligonucleotides—on the order of 100,000 probes—located every 30 Kb or so. These oligonucleotides, which are short subsequences of hundreds of base pairs or even smaller, are from regions of the genome that do not share homologous sequences elsewhere in the genome, so each probe is likely to occupy a unique position in the normal genome, and likely has exactly two copies. One such oligonucleotide may belong to a region in the cancer genome that has an altered copy number, e.g. c, $0 \leq c \neq 2$. When the cancer genome is sampled, this oligonucleotide would likely occur with a probability that is c/2 times that in the normal genome. Thus, the copy number can be computed by a ratiometric measurement of the abundance of an oligonucleotide in cancer sample measured against that in the normal genome. The ideas described for a single oligonucleotide can be generalized to measure the copy number variations for all the probes simultaneously with high-throughput microarray experiments. While the ratiometric measurements and normalizations may minimize the multiplicative noise in the system, a large amount of uncharacterized noise, mostly additive, remains that may render the data worthless without the use of a proper data-analysis procedure. Furthermore, since the data may come from multiple sources, collected with varying protocols and subjected to vagaries of the technologies employed for its collection, the procedure should be general, and based on a minimal set of prior assumptions regarding the methods.

SUMMARY OF THE INVENTION

The present invention relates to systems, methods and software arrangements for the detection of variations in the copy number of a gene in a genome. These systems, methods and software arrangements are based on a simple prior model that uses a first process generating amplifications and deletions in the genome, and a second process modifying the signal obtained to account for the corrupting noise inherent in the technical methodology used to scan the genome. A Bayesian approach according to the present invention determines, e.g. the most plausible hypothesis of regional changes in the genome and their associated copy number (i.e. their deviation from a normal distribution). The systems, methods and software arrangements according to the present invention can be framed as optimization problems, in which a score function is minimized. This score function assigns penalties of different types for each type of deviation from a normal distribution (e.g. breakpoints, unexplainable probe values, noise, etc.). Furthermore, the score function can be linear with respect to the type of penalty assigned, and may satisfy a weak form of "principle of optimality," thus allowing an efficient dynamic programming implementation. The systems, methods and software arrangements of the present invention may be useful to assist in the scientific study, diagnosis and/or treatment of any disease that has a genetic component, including but not limited to cancers and inherited diseases.

For example, according to certain exemplary embodiments of the present disclosure, a storage medium can be provided for storing a software program that can be adapted (e.g., configured) for detecting at least one variation in a numerical data ordered sequentially from data contained in at least one dataset. The exemplary software program, when executed by a processing arrangement, can be configured to cause the processing arrangement to execute operations (e.g., procedures), including receiving the at least one dataset which can include sequential data, receiving prior information of statistical character associated with the dataset(s) in a form of models of probability distributions, partitioning sequential data into non-overlapping intervals, providing further information for each of the intervals, and determining whether at least one of the intervals is provided within the at least one dataset so as to indicate the at least one variation in the numerically ordered data. Thus, it is possible to determine an indication of the at least one variation in the numerically ordered data based on further information associated with at least one of each of the intervals.

According to further exemplary embodiments of the present disclosure, the sequentially ordered numerical data contained in at least one dataset can include (i) vectors of identical dimensions, (ii) numbers and/or (iii) sequences of numbers of identical length. The exemplary software program can be further configured to cause the processing arrangement to obtain the sequential data by analyzing biological markers. The sequential data can be obtained using (i) micro-arrays and/or (ii) techniques which can manipulate single molecules at a time.

The prior information can contain states, state transitions, probability distributions over states, and/or conditional probability distributions over possible state transitions for all given current states, for example. The sequential data can include (i) vectors of identical dimensions, (ii) numbers, (iii) sequences of numbers of identical length, and/or (iv) biologically relevant local parameters. The states of the prior information can contain loss of heterozygosity ("LOH") information. Further, the states of the prior information can include, e.g., a regular state and/or a deviated state, be included in each of the intervals.

The software program according to particular exemplary embodiments of the present disclosure can be further configured to cause the processing arrangement to examine a quality of at least one result obtained in the performance of certain procedures described herein above, such as the partitioning of sequential data into non-overlapping intervals, providing further information for each of the intervals, and determining whether at least one of the intervals is provided within the at least one dataset so as to indicate the at least one variation in the numerically ordered data. Further, the result can be evaluated according to certain criteria, including, e.g., (i) a goodness of fit which can determine a quality of estimated parameters in each of the intervals plausibly generating the data therein, and/or (ii) a prevention from overfitting such that successive non-overlapping intervals can have substantially-separated parameter values. For example, the appropriateness of fit in each of the intervals can be obtained by taking (a) an average squared deviation of data samples in the respective interval, (b) a square root of the average squared deviation of the data samples in the respective interval, and/or (c) an average absolute deviation of data samples in the respective interval.

According to still another exemplary embodiment of the present disclosure, provided is a storage medium storing a software program that can be adapted (e.g., configured) for detecting variations in genome copy number in one or more genetic samples from data contained in at least one dataset. For example, the software program, when executed by a processing arrangement, can be configured to cause the processing arrangement to execute certain operations (e.g., procedures), including receiving the at least one dataset, and/or partitioning the genomes of the genetic sample(s) into non-overlapping intervals from the at least one dataset. The non-overlapping intervals, such as the presence thereof within the at least one dataset, can be indicative of at least one variation in the genome copy number in the genetic sample(s). The data contained in the dataset(s) can be obtained by analyzing the genetic samples with a plurality of genetic probes. The partitioning of the genomes of the genetic sample(s) can be performed by selecting an interval structure for the at least one dataset that maximizes a likelihood function. For example, the likelihood function can be provided as $$L(\langle i_1, \mu_1, i_2, \mu_2, \ldots, i_k, \mu_k \rangle) =$$

-continued $$e^{-p_b N} \frac{(p_b N)^k}{k!} \cdot \frac{1}{(2\pi\sigma^2)^{\frac{n}{2}}} \cdot \prod_{i=1}^{n} e^{-\frac{(x_i - \mu_j)^2}{(2\sigma^2)}}.$$

$$p_e^{\# \ global}(1 - p_e)^{\# \ local},$$

where #global is a number of "normal" probes with the global mean, #local is a number of remaining probes, $p_r$ is a probability that a particular probe is normally distributed, $p_b N$ is a Poisson parameter, $\mu$ is the estimated sample mean for the interval, and $\sigma$ is the standard deviation of the sample.

The partitioning can be performed by selecting an interval structure for the at least one dataset that minimizes a negative log likelihood of a likelihood function. For example, the negative log likelihood can be provided as $$-\log L(I') = -\log L(I) +$$

$$\frac{1}{2\sigma^2} \sum_{j=i_k+1}^{i_{k+1}} (x_j - \mu_{k+1})^2 -$$

$$\log(p_b N) +$$

$$\log(k + 1) +$$

$$\frac{i_{k+1} - i_k}{2} \log(2\pi\sigma^2) -$$

$$(i_{k+1} - i_k) \begin{cases} \log p_e \\ \log(1 - p_e) \end{cases}$$

wherein $i_k+1$ to $i_{k+1}$ is included only if the added interval extending from $i_k+1$ to $i_{k+i}$ is global.

According to certain exemplary embodiments of the software arrangement, the selection of an interval structure can be performed by computing an optimality property satisfied by the negative log likelihood function according to the formula $$Opt_n = \underset{l \in Working\ Set_x}{\arg\min} (-\log L(1)),$$

wherein Working Set$_n$=

$$\bigcup_{i<12} \{Opt_i \ o(n, \mu_e), Opt_i \ o(n, \text{mean}(x_{i+1}, \ldots, x_n))\}.$$

According to yet another exemplary embodiment of the present disclosure, provided is a storage medium storing a software program that can be adapted (e.g., configured) for detecting at least one variation in genome copy number in one or more genetic samples from data contained in at least one dataset. For example, the software program, when executed by a processing arrangement, can be configured to cause the processing arrangement to receive the dataset(s) and/or partition the genomes of the genetic sample(s) into non-overlapping intervals from the dataset(s). The non-overlapping intervals, such as the presence thereof within the at least one dataset, can be indicative of at least one variation in the genome copy number in the genetic sample(s).

These and other objects, features and advantages of the present disclosure will become apparent upon reading the following detailed description of exemplary embodiments of

DETAILED DESCRIPTION OF THE INVENTION

I. First Exemplary Embodiment

A. Exemplary Model

Figure 1:
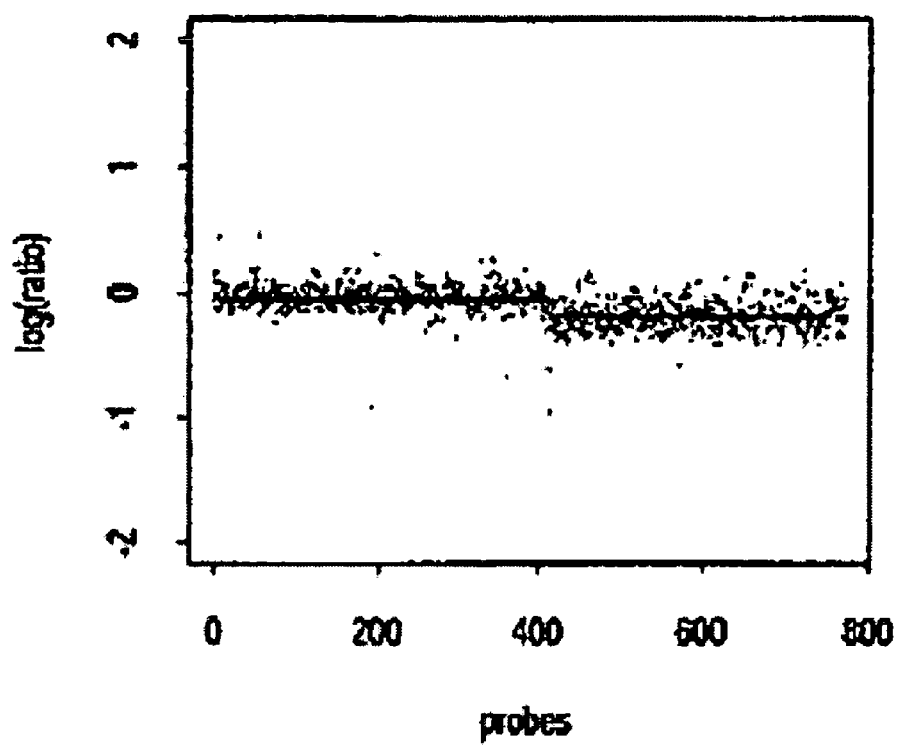
FIG. 1 shows exemplary segmented probes on ROMA data, chromosome 2. $p_r$=0.55, $p_b$=0.005, shrinkage=0.9.

A probabilistic generative model for observed copy number data is described herein below. The exemplary model is a Bayesian-type model, in that it employs parameterized prior distributions, and uses the posterior distribution function to estimate the underlying model. The kinds of prior models considered, however, may preclude the use of Bayesian estimators. Thus, a maximum a posteriori (MAP) framework was used to estimate the underlying model.

Prior Structure in the Probabilistic Model

The statistical model generally only takes into account the major sources of copy number variation in an abnormal genome. It is described by the two scalar parameters $0 \leq p_r$, $p_b \leq 1$ and captures a few essential aspects of the true biological mechanisms.

Such a model assumes that there is a normal copy number distribution for probes, and that the probability for a particular probe being normal is $p_r$ (for explained probability). If a probe is normal, it is assumed that its measured copy number is distributed according to a Gaussian distribution with mean $\mu_e$ and standard deviation $\sigma_e$.

The model also assumes that there may be hotspots in the genome that are more susceptible to amplification events (also known as duplication events) or deletion events. It is possible to model the number of mutation events as a Poisson process. The parameter $p_b$, the average number of intervals per unit length, describes such a Poisson process. In other words, if N is the length of the genome (i.e. total number of probes), then the number of intervals is a Poisson distribution with mean and variance equal to $p_b N$ (the Poisson parameter).

Given the raw copy number readings for N probes arranged on the genome, it can be assumed that the genome is subdivided into k non-overlapping intervals. All probes belonging to any particular interval likely have a similar evolutionary history in that they have participated in the same duplication and deletion events. The number of intervals into which the probes can be separated represents a measure of evolutionary progress (e.g., of the cancer cell line). Substitution and other mutation events may be ignored for the purposes of this model. This under-modeling reveals itself as extra noise in the copy number data. Thus, in such an exemplary model, each interval in this subdivision has a "true" copy number. One object of the exemplary system of the present invention is to estimate the correct subdivision and copy numbers associated with each sub-interval. Despite its simplicity, the model may be used as the basis of a statistical process to infer the aberrations without overfitting the data.

In particular, given a set of N probe copy number values arranged on the genome, it can be assumed that there is an unknown partition of this set into non-overlapping sub-intervals. The probe copy numbers in the j-th interval may be assumed to arise as independent samples from a Gaussian distribution N ($\mu_j$, $\sigma_j$). Thus, the data relating to the j-th interval can be represented as the tuple $I_j = (\mu_j, i_j, \sigma_j)$, where $\mu_j$ and $\sigma_j$ are the mean and standard deviation of the appropriate Gaussian distribution, and $i_j$ the position of the last probe in the interval. The set of intervals $I = \{I_j | j=1 \ldots k\}$ is called an interval structure.

Another object of the exemplary system of the present invention is to partition a given sequence of probe copy number values into an interval structure I. Probes in each interval may be assumed to be samples from the same Gaussian distribution. The input is a sequence of N values $\{v_i, i=1 \ldots N\}$. The output, an interval structure $I_N$, is a partition of the probes into k non-overlapping intervals.

Likelihood Function

The two parameters $p_r$ and $p_b$ can specify the prior distribution. To simplify what follows, it can be assumed that all the standard deviations are known and have a common value denoted by $\sigma = \sigma_e$.

The prior distribution on the set of interval structures is defined by, $$Pr(\langle i_1, \mu_1, i_2, \mu_2, \ldots, i_k, \mu_k \rangle) = e^{-p_b N} \frac{(p_b N)^k}{k!} p_e^{\#global} (1-p_e)^{\#local}, \quad (1)$$

where #global is the number of "normal" probes with the global mean and #local is the number of remaining probes. In each interval $I_j$, the data points can be modeled by adding independent Gaussian noise to this prior structure, and are drawn from the Gaussian distribution N ($\mu_j$, $\sigma$).

The likelihood function for the first n probes is given by $$L(\langle i_1, \mu_1, i_2, \mu_2, \ldots, i_k, \mu_k \rangle) = \qquad (2)$$
$$e^{-p_b N} \frac{(p_b N)^k}{k!} \cdot \frac{1}{(2\pi\sigma^2)^{\frac{n}{2}}} \cdot \prod_{i=1}^{n} e^{-\frac{(x_i-\mu_j)^2}{(2\sigma^2)}} \cdot p_e^{\#global}(1-p_e)^{\#local},$$

where $i_k = n$ and i belong to the jth interval.

A MAP solution to the segmentation problem may consist of selecting the interval structure I * that maximizes this likelihood function, or similarly, minimizes the negative log likelihood of L. In the above expression for L, only the $\mu$ values of non-global processes are unknown and these values are estimated by using the sample mean for the interval.

B. Exemplary Process and Implementation

A dynamic programming process (or algorithm) can be used to minimize the above negative log likelihood function. Starting with an interval structure $I = \langle i_1, \mu_1, \ldots, i_k, \mu_k \rangle$, the structure can be extended to the interval structure $I' = \langle i_1, \mu_1, \ldots, i_{k+1}, \mu_{k+1} \rangle$, where $i_{k+1} > i_k$. This operation is denoted as $I' = I \circ (i_{k+1}, \mu_{k+1})$. The following result can be used to compute the log likelihood for such an extension:

$$-\log L(I') = -\log L(I) + \frac{1}{2\sigma^2} \sum_{j=i_k+1}^{i_{k+1}} (x_j - \mu_{k+1})^2 - \log(p_b N) + \quad (3)$$

$$\log(k+1) + \frac{i_{k+1} - i_k}{2} \log(2\pi\sigma^2) - (i_k - i_k) \begin{cases} \log p_e \\ \log(1 - p_e) \end{cases},$$

where the last term on the right side is chosen according to whether the last added interval (e.g., a term extending from $i_k+1$ to $i_{k+1}$) is "global" or not.

An exemplary dynamic programming process for MAP estimation is described as follows. An optimal interval structure covering the first n probes is provided. Let the [m+1, n] be the last interval in this structure. The remaining intervals in the interval structure comprise an optimal interval structure covering the first m probes. To compute the optimal interval structure on the first n probes, extensions of the optimal structures covering i probes can be considered, for all i<n.

For example, let $Opt_n$ be the optimal choice of $I_k$ for the first n data points where $n=i_k$. $Opt_1$ is easy to compute using a case-by-case analysis, as the only choice needed to be made is whether the sole interval is local or global.

The set of all extensions of smaller optimal fragments is denoted as $$\text{Working } Set_n = \bigcup_{i<n} \{Opt_i \circ (n, \mu_e), Opt_i \circ (n, \text{mean}(x_{i+1}, \ldots, x_n))\}. \quad (4)$$

With this notation, the optimality property satisfied by the negative log likelihood function can be expressed as $$Opt_n = \underset{I \in \text{Working } Set_n}{\arg\min} (-\log L(I)).$$

Since I is of the form of an extension, its value can be calculated iteratively using equation 3, thus leading to a dynamic programming algorithm.

C. Results

The performance of this Bayesian scheme has been evaluated using three kinds of data. In each of these datasets, it can be observed that the proper choice of the parameter values $p_r$ and $p_b$ generally leads to good segmentation. In fact, there is a fairly large region of the "$p_r$-$p_b$ space" that leads to good segmentation, and thus the procedure is stable over a large domain. As $p_b$ is increased, the optimal segmentation accumulates more and more segments. As $p_r$ is increased, there are more probes with the global mean and thus the number of different segments tend to reduce. Furthermore, the bias in the solution in each interval increases. Thus, the effects of $p_r$ and $p_b$ generally oppose each other, and this leads to complicated behavior outside the domain of stability.

Two other parameters that affect the segmentation are the global mean, $\mu_e$ and the (common) standard deviation $\sigma$. A proper choice of $\mu_e$ is critical, as it controls the bias in the segmentation. Increasing $\sigma$ tends to weaken the influence of the data on the segmentation obtained. This is because the posterior distribution tends to the prior distribution as $\sigma \to \infty$.

ROMA Data from Breast Cancer Cell Lines

ROMA (representational oligonucleotide microarray analysis) is a comparative genomic hybridization (CGH) technique developed by Wigler et al. at Cold Spring Harbor Laboratory (see Lucito et al., 2000, *Genome Research*, 10(11):1726-1736). ROMA evolved from an earlier method, representational differential analysis (RDA), by adapting RDA for vastly higher throughput with an oligonucleotide microarray. For this purpose, ROMA uses a comparative "two-color" scheme to compare multiple genomes, each represented with reduced complexity derived with a PCR-based method. See Lisitsyn et al., 1993, *Science* 258:946-951; Lucito et al., 1998, *Proc. Natl. Acad. Sci. USA* 95:4487-4492. As in other array-based methods, ROMA performs simultaneous array hybridization to detect a "normal" genome at one fluorescent wavelength and an abnormal genome at another. Researchers have convincingly demonstrated that complexity reduction of samples by representation improves signal-to-noise performance (i.e. small $\sigma$'s in the model described herein), and diminishes the amount of sample required for analysis. See Lucito et al., 2000, *Genome Research* 10:1726-1736. Representations used by ROMA are based on amplification of short restriction endonuclease fragments, and hence are predictable from the nucleotide sequence of the genome. The exemplary system of the present invention has been tested on the datasets from the Wigler laboratory obtained by ROMA from the genomes of breast cancer cell lines. The exemplary datasets are based on 85,000 well-characterized probes, each 70 bp in length, providing a resolution of one probe every 15-30 Kb.

Figure 2:
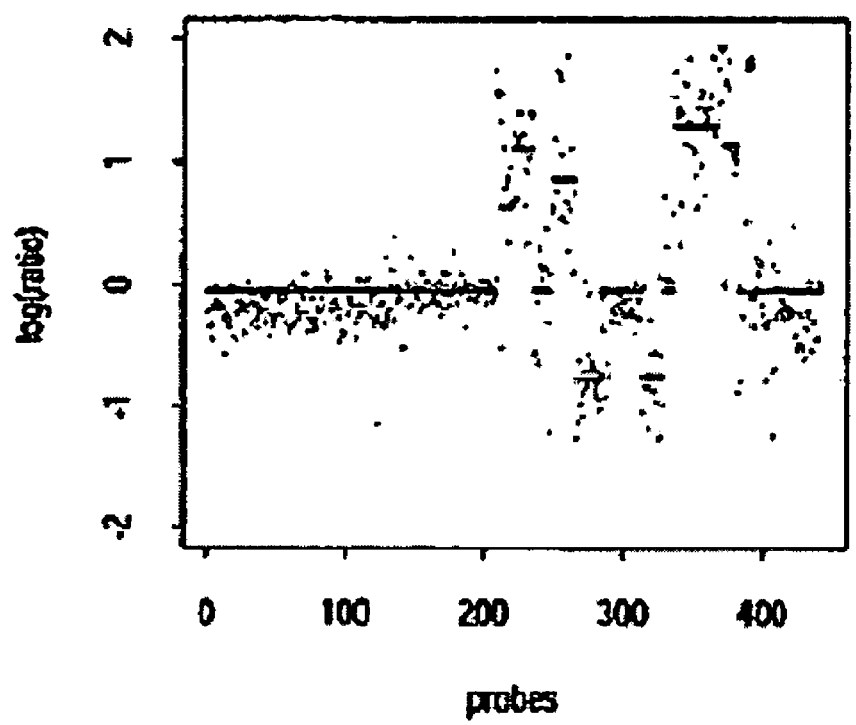
FIG. 2 shows exemplary segmented probes on ROMA data, chromosome 8. $p_r$=0.55, $p_b$=0.01, shrinkage=0.9.

FIGS. 1 and 2 show graphs displaying ROMA breast cancer data from chromosomes 2 and 8, respectively. The data have been analyzed, and the segmentation ascertained by the instant system is indicated by the straight lines laid overtop of the individual data points. In this dataset, low-complexity representation together with a careful choice of probes led to data with low noise, Thus, it is possible to set $\sigma$ to be the sample standard deviation of the total data, and obtain good performance. Because of the structure of the data in chromosome 2, additional biological knowledge should be used to determine the value of the global mean. However, using the knowledge that the global mean is close to 0, the system of the present invention reveals the presence of a large deletion in chromosome 2 from this dataset.

ArrayCGH Data from Prostate Cancer Cell Lines

In contrast to conventional CGH, arrayCGH is a recently developed technique that maps the duplicated or deleted chromosomal segments onto high-density arrays of well-characterized bacterial artificial chromosomes (BACs), rather than onto metaphase chromosomes. This method has been used for fine-mapping duplications and deletions occurring in cancers and other human diseases, including birth defects and mental retardation. See Albertson and Pinkel, 2003, *Hum. Mol. Genet.* 12(Suppl 2):RI45-52 for a review and applications of this technique. Among the tumors that have been studied are breast, head and neck, Wilm's, esophageal, pulmonary artery intimal, adrenocortical, renal and prostate cancers and lymphomas. The system of the present invention has been applied to a dataset obtained by high-resolution arrayCGH analysis of prostate cancer tissue. The 32K BAC array implemented by a group in Nijmegen covers over 99.97% of the sequenced human genome, and has a theoretical resolution of 46 kB.

Figure 3:
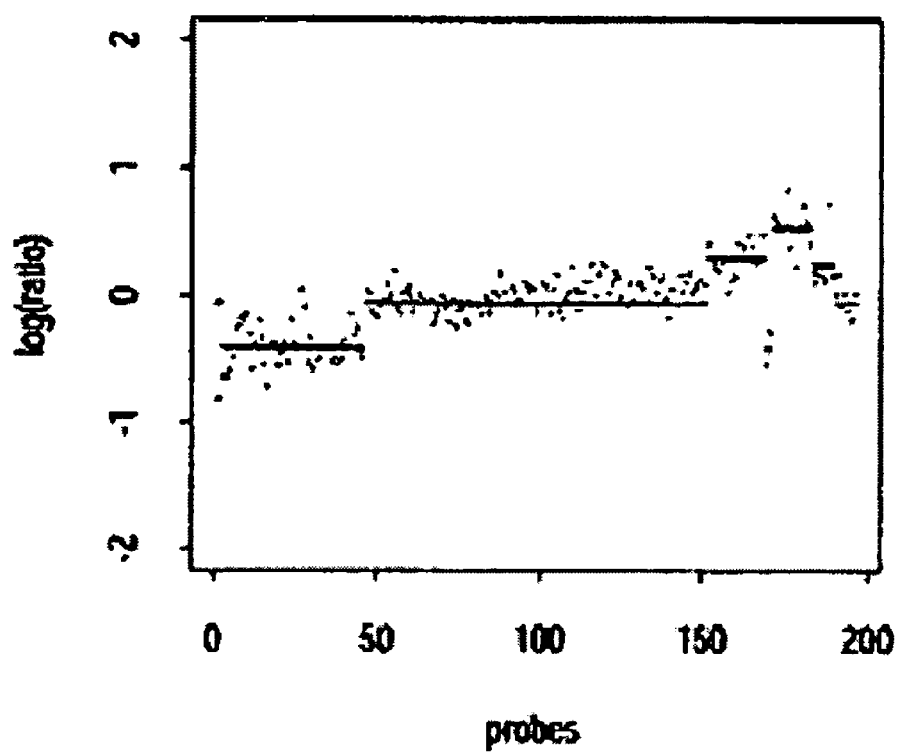
FIG. 3 shows exemplary segmented probes on arrayCGH data, chromosome 8. $p_r$=0.55, $p_b$=0.005, shrinkage=0.9.

FIG. 3 shows a segmentation of probes produced by the application of the system of the present invention to data from prostate cancer cell lines obtained through arrayCGH experiments. These data exhibit greater noise than the ROMA data. However, despite the increased noise, the system of the present invention yields reasonable segmentations.

Simulated Data

Cancer-driven fluctuations in genetic copy number have many mechanisms. While the details thereof vary considerably, there is an overall similarity between them. This type of biologically-inspired model has been used to generate synthetic data to test the segmentation system according to the present invention. This generative model is distinct from the prior model (see Equation 2) used in the segmentation algorithm. However, it can use parameters $p_r$ and $p_b$ with similar meanings, so that the effect of misestimation of $p_r$ and $p_b$ may be easily studied.

Simulation Procedure

The genetic evolutionary process is modeled using hotspots. These hotspots are points on the normal genome that are more susceptible to duplication and deletion events. In the simulated copy number data, hotspots are uniformly located over the genome such that the probability of a break is given by $p_b$. Such hotspots are considered to be the starting points for a given duplication or deletion event. For each of these hotspots, a new copy-number value that represents the mean for the new interval is assigned. The mean values are drawn from a power transformed gamma distribution. The length of the intervals follows a geometric distribution such that the ratio of expected fragment length and the expected inter-hotspot distance is $p_r$. Once the segmentation and the mean values are thus selected, the simulated data may be generated by adding random Gaussian noise to the mean values. It is possible to enhance this model to incorporate repeated indel events, with some "stickiness" of the hotspots, as can be observed in practice. However, even the simple model described immediately above captures most statistical features of real genomes.

Figure 4:
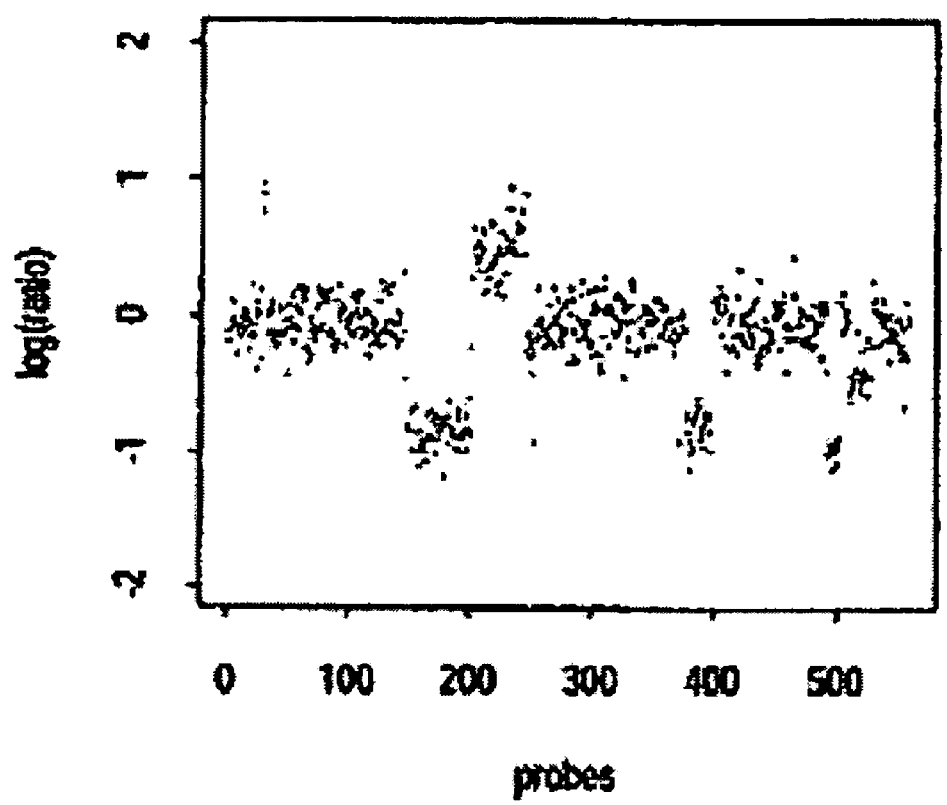
FIG. 4 shows an exemplary simulated genome with $\mu$=0.0 and $\sigma$=0.15.

The simulated genome show in FIG. 4 may be compared to the similar ROMA data shown in FIG. 2.

Effect of Noise on Performance

Figure 5:
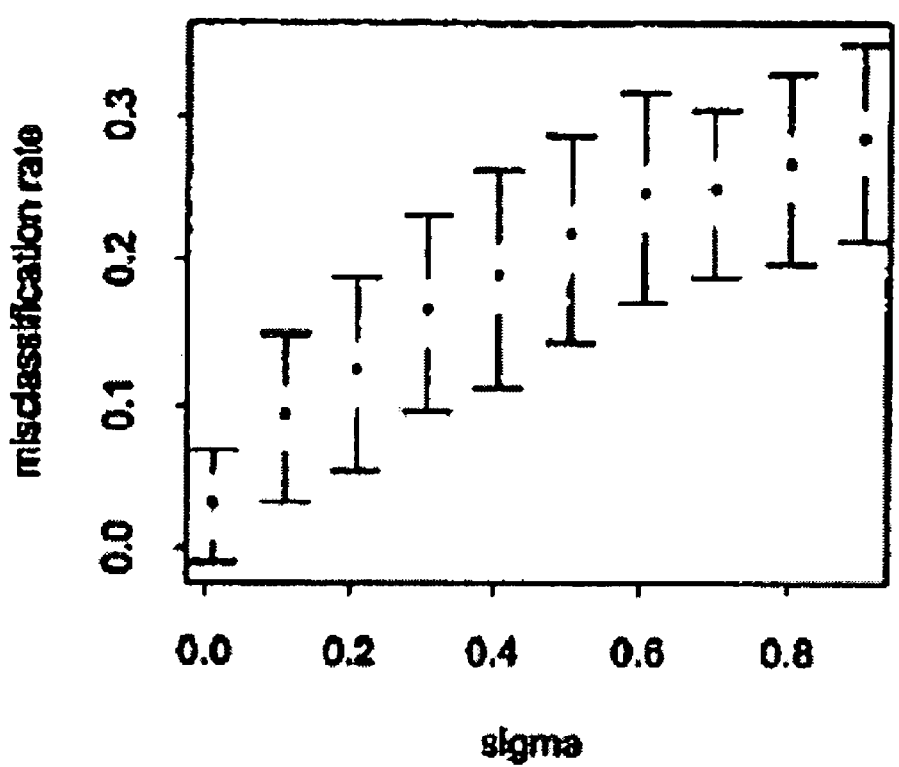
FIG. 5 shows an exemplary average number of misclassified probes plotted against increasing $\sigma$ on synthetic data, with the average number of misclassified probes over 100 trials being normalized against the length of the simulated genome.

The effect of increasing the $\sigma$ of the underlying model on the performance of the segmenter has been investigated. Assuming that the parameters of the model are correctly estimated, the segmenter can output the estimated mean value at every probe position. Using the known mean values, these two sequences of means can be compared. In this setting, a good measure of error is the number of misclassified probes. Thus, the number of probes which were actually normal, but have been classified as amplified or deleted and vice versa are counted. FIG. 5 shows that the rate of misclassification increases as $\sigma$ increases, as would be expected.

D. Prior Selection and Performance Evaluation

Introduction

Proper selection of the prior distribution has received extensive attention in the literature. Approaches include non-informative priors (Jeffreys, 1946, *Proceedings of the Royal Society of London (Ser. A)* 186:453-461), reference priors (Bernardo, 1979, *Journal of Royal Statistical Society (Ser. B)* 41:113-147; see also Berger & Bernardo, 1992, *In Bayesian Statistics* 4, Berger et al. (eds), Oxford University Press, Oxford, pp. 35-60 and Kass & Wasserman, 1996, *Journal of the American Statistical Association* 91:1343-1370), and conjugate priors (Raiffa & Schlaifer, 1961, *Applied Statistical Decision Theory*. Division of Research, Graduate School of Business Administration, Harvard University), among others. Conjugate prior methods frequently arise in connection with exponential families of distributions. See Brown, 1986, IMS Lecture Notes, Monograph Series 6. Hayward, Calif. Other approaches include using invariance properties to posit prior distributions with good performance. More recent and somewhat more data-dependent techniques include hierarchical Bayes techniques and empirical Bayes techniques. Textbooks such as those by Bernardo and Smith (*Bayesian Theory*. Wiley, New York, 1994), Berger (*Statistical Decision Theory and Bayesian Analysis*. 2nd edition, Springer-Verlag, New York, 1985), Carlin et al. (*Bayes and Empirical Bayes Methods for Data Analysis*. Chapman & Hall, London, 1996), Gelman et al. (*Bayesian Data Analysis*. Chapman & Hall, London, 1995) and Robert (*The Bayesian Choice*. Springer, New York, 2001) describe model selection as a part of Bayesian learning.

For the problem of estimating the probe copy numbers, the prior distribution is specified by the two probability parameters, $p_r$ and $p_b$. The other parameters ($\mu$, the global mean and $\sigma^2$, the global variance) can be estimated from experiments. The problem of prior selection reduces to the problem of optimally selecting the values of $p_r$ and $p_b$. A large class of approaches to this estimation process hinges on preventing over-fitting of the data.

Two distinct criteria are presented herein for estimating the correct prior values given a set of probes in the same general framework. One is the minimax approach, which is well known in statistical literature. Also described herein is another approach according to the present invention, based on statistical decision theory, which directly controls the level of over-fitting.

The first (minimax) approach searches for values of $p_r$ and $p_b$ which minimize the maximum value of the likelihood function (Equation 3). The minimax criterion is pessimistic, in that it selects the prior which generates the worst likelihood value. See e.g. Brown, 1971, *Annals of Mathematical Statistics* 42:855-903; Strawderman, 1971, *Annals of Mathematical Statistics* 42:385-388; Strawderman, 1974, *J. Multivariate Anal.* 4:255-263; Berger, 1985, *Statistical Decision Theory and Bayesian Analysis*, 2nd edition. Springer-Verlag, New York; Brown, 1993, In *Statistical Decision Theory and Related Topics* 5, Gupta and Berger (eds), Springer-Verlag, New York, pp. 1-18; Brown 2000, *Journal of the American Statistical Association* 95:1277-1282; Strawderman, 2000, *Journal of the American Statistical Association* 95:1364-1368.

The second approach, described herein, relies on the fact that, in any segmentation, each jump comprises a separation of the probes in the two adjoining intervals. Thus, if a segmentation is over-fitted, at least one of its jumps also should be over-fitted. Hotelling's $t^2$ statistic can be used at each jump to compute a measure of this over-fitting. See Anderson, 1958, *An Introduction to Multivariate Statistical Analysis*, Wiley, New York or Wilks, 1962, *Mathematical Statistics*. Wiley, New York.

The F-test on Hotelling's $t^2$ statistic can be used to test if two sets of independent samples come from populations with the same mean, assuming that they have the same (but still unknown) variance. Thus, let $x_1, x_2, \ldots, x_{N_1}$ and $y_1, y_2, \ldots, y_{N_2}$ be the two sets of in dependent samples from successive intervals of size $N_1$ and $N_2$, respectively. Then the statistic:

$$T^2 = \frac{\frac{N_1 N_2}{(N_1 + N_2)}(\bar{x} - \bar{y})^2}{\frac{1}{df_1 + df_2}\left(\sum_i (x_i - \bar{x})^2 + \sum_j (y_j - \bar{y})^2\right)},$$

is defined where $\bar{x}$ and $\bar{y}$ are the respective sample means, and $df_1$ and $df_2$ refer to the respective degrees of freedom of the two samples. Under the null hypothesis (of equal means), the $t^2$ follows an F distribution with 1, $(df_1+df_2)$ degrees of freedom. This leads to a one-tailed F-test.

Intuitively, $t^2$ should be made large to avoid over-fitting. The cumulative probabilities for the appropriate F distribution determine how large $t^2$ should be.

Evaluating Segmentation Processes

Performance of segmentation processes, in general, can be understood in terms of overfitting. As the sizes of the individual blocks become smaller, the size of the residue is reduced. Thus, by overfitting, any algorithm may explain the data very well. To determine if the data have been overfitted, the distribution of the "jumps," i.e. the absolute magnitudes of the difference of the levels of successive blocks, may be examined. Data which is not overfitted will have a series of larger jumps.

In the process described herein, this behavior can be understood by studying the effect of $p_b$ on the computed interval structure. At values of $p_b$ near 1, too many breaks tend to be inserted into the interval structure. There are many (incorrect) breaks with very low jump values. Furthermore, the jump values for the correct breaks tend to split up into several (smaller) jumps. As the $p_b$ value decreases, the number of small jumps decreases. The point where it first disappears is when the algorithm stops overfitting. Further decreases in $p_b$ result in too few breaks, reflected in the residue growing larger.

The F-test described above may be used to establish an independent criterion with which to judge the efficacy of segmentation algorithms. For any segmentation, the F-test may be applied on the jumps of the segmentation. For each such jump, the $t^2$ statistic is computed and hence the p-value, which is the cumulative probability of the appropriate F-distribution up to the $t^2$ value. This quantity is the probability that the $t^2$ value could have been obtained by chance if the break had been incorrect. The minimum of these p-values over the set of jumps in the segmentation is determined, and this minimum p-value is the single number used to judge the quality of the solution.

After extensive empirical testing, the F-test criterion described above has been shown to produce values for the prior parameters ($p_r$ and $p_b$) similar to those obtained under the minimax criterion.

The approach described hereinabove extends to multi-dimensional datasets mutatis mutandis. For multi-dimensional datasets, the relevant likelihood function should be changed to the following $$L(\langle i_1, \mu_1, i_2, \mu_2, \ldots, i_k, \mu_k\rangle) = $$

$$e^{-p_b N}\frac{(p_b N)^k}{k!} \cdot \frac{1}{(2\pi|\Sigma|)^{\frac{n}{2}}} \cdot \prod_{i=1}^{n} e^{-(z_i-\mu_i)'\Sigma^{-1}(z_i-\mu_j)/2} \cdot p_e^{\#global}(1-p_e)^{\#local},$$

The $t^2$ statistic can be modified similarly.

II. Second Exemplary Embodiment

A. Overview

Generally, somatic genomic alterations MAY be inferred using any of the many whole-genome microarrays: e.g., BAC Arrays, ROMA (Nimblegen), Agilent and Affymetrix chips, they appear to require varying algorithmic approaches in data-clean-up, noise-removal, background-correction, and normalization. In particular, the Affymetrix gene-chip technology has proven richer, but more recalcitrant than the rest, as Affymetrix technology faces many fundamental difficulties. Some exemplary difficulties include a large fraction of unusable mismatch probes, wild statistical variations from one experiment to another, noise introduced by PCR process and cross-hybridization, polymorphic variations in biallelic data, and most importantly, wide-variability in the thermodynamic properties of multiple probes in a probe set. The exemplary embodiment may employ a statistical algorithm to tame such corrupting noises through a systematic but incremental characterization of noise and probe affinities, typically without requiring any extraneous calibrating experiments. The embodiment, while analyzing the current experimental data, may first assume that the earlier data have been analyzed with some degree of accuracy, with the corresponding copy numbers, probe affinities, normalizing statistics, noise processes, etc., all well characterized. Using the earlier data and priors based on their statistics, the embodiment may simultaneously solve for the probe affinities and the copy-numbers in two stages: first, by minimizing a weighted sum-of-square error function; and second, further improving the copy-number statistics through a segmentation algorithm. In the process, it continues to improve all the relevant statistics with each successive experiment.

B. Introduction

Somatic genomic alterations, including allelic loss and gene amplification, are targets of intense studies since may contribute to the development of various forms of cancer. Loss of heterozygosity (LOH) and comparative genomic hybridization (CGH) studies have led to the identification of a number of recurrent chromosomal imbalances in cancer genome. For instance, several genetic studies have identified allelic losses in prostate cancer genomes for alleles at 1p36, 3p12-q22, 3p24-26, 6q14-q21, 7q31, 8p21-p22, 10q23-q25, 11p15, 11p12, 11q22, 11q23-q24, 13q14, 16q22, 17p, 17q21, and Xq11-q13. Furthermore, several recent studies have indicated that copy-number polymorphisms (e.g., variations in the copy number of large segmental genomic insertions and deletions within a population) are more common than previously believed. Additionally, similar variations across the genomes in different cells within a single organism may not be uncommon; better understanding of these variations and their causative mechanisms may shed light on the processes involved in aging and disease progression. Other alterations of similar nature in germ-lines may lead to a better understanding of autism, schizophrenia, and other childhood diseases.

In contrast to conventional CGH, arrayCGH is a recently developed technique that maps the duplicated or deleted chromosomal segments onto high-density arrays of well-characterized bacterial artificial chromosomes (BACs), e.g., BAC-arrays, or oligonucleotide arrays, e.g., Nimblegen-based maskless arrays such as ROMA, and whole genome polymorphism chips, e.g., Affymetrix SNP Chips. Statistically robust data analysis methodologies may play a role in assigning correct copy number values to each genomic region despite the various unmodeled noise processes inherent to the underlying technology, clinical protocols and biological processes.

Briefly speaking, noise reduction is based on several technological as well as statistical approaches: (1) probe selection and protocol; (2) genomic complexity reduction; (3) background calibration; (4) normalization; and (5) segmentation. Usually steps (1) and (2) are determined by the developer of the technology and by the biochemical protocol employed. However, these operations affect the manner in which the statistical method may attempt to remove noise, and become absolutely critical, in the context of analyzing chips that additionally employ multiple probes in a probe-set covering multiple allelic forms. Such an approach is exemplified, for example, by the Affymetrix chips, and may lead to further complications involving statistically sophisticated algorithms, as explained herein. Furthermore, these approaches often involve integrated, but subtle, interplay among the last three listed operations: background-correction, normalization and segmentation. In particular, described herein are processes leading to non-uniform background noise, caused by non-specific hybridization, as well as variations within a probe-set, caused by entropic structure of the perfect-match and mismatch probes that can be selected at a particular genomic location. By creating a design space whose orthogonal components are the algorithms for background correction or algorithms for group summarization (normalizing the within-group-variation in a probe-set), an exemplary embodiment may enumerate a large class of possible statistical algorithms.

C. Microarray Technology

Advanced oligonucleotide-based microarrays or gene-chips, e.g., Affymetrix gene-expression and mapping chips, typically consist of markers placed on a rectangular surface for hybridization experiments. Each marker region of interest generally is covered by a fixed number (20 for the 10K and 100K mapping arrays, but possibly, a variable number ranging between 12 and 20 for 500K arrays) of perfect match (PM) probes at varying (but small) offsets, and an equal number of corresponding mismatch (MM) probes. The possible probes cover all or most sources of variation, including position (offset), strand direction (sense or anti-sense), as well as two possible alleles in the case of the mapping arrays. The collection of probes used to query a given marker region of interest is referred to as a probe-set. Generally, the probes in a probe-set do not all have similar responses. Exacerbating the matter, it is possible that, for a significant fraction (about 30%) of probes in a probe-set, the mismatch probes may exhibit higher intensity than their associated perfect-match probes. This may be a counter-intuitive situation that may most likely be explained through the stacking properties of a probe and its effect on changes to local torsions and hybridization avidity. For these reasons, such probes should be treated as "missing data" and handled carefully, or be evaluated by statistical methods that work only with perfect-match probes. These problems may lead to particularly difficult situations in regions of hemizygous or homozygous deletions, and thus prominently in regions containing loss of heterozygousity.

Nonetheless, the responses of a group of probes in a probe-set are not necessarily all random. For instance, even when the genome is treated with different experimental conditions, the rank ordering of the responses of the different probes in the probe-set tends to stay relatively fixed, independent of the condition of the experiment, the relative abundance of RNA molecules, or DNA copy numbers. This effect has its explanation in differing but fixed affinities of the different probes in the probe-set to the same amount of signal.

Other complex processes may corrupt the latent signal. Well known examples are the noise from the optical subsystem, consisting of the laser-scanner, image registration, computation of integrated intensity, etc., that "read" the hybridized chip, and the presence of a large amount of non-specific cross-hybridization from other unrelated areas of the genome with some homology to some probes in the probe-set. As cross hybridization arises from unwanted hybridizations between querying probes and targets, which are only approximately complementary, they may vary widely from one genomic region to another. One method to improve signal to noise ratio, with reduced cross-hybridization, is through "complexity reduction," which subsamples the genome by cutting the genome with a relatively rare-cutting restriction enzyme and only amplifying short restriction fragments from the tail of their distribution with a suitable choice of adapters and PCR primers. In these cases, the probe-sets typically are only selected from the unique regions of these short restriction fragments and are hybridized on the chip with parallel reduced-complexity representations from either experimental (e.g., cancer) or control (e.g., normal) genomes. However, this process generally depends on variations of base-specific amplification efficiencies, specificity of restriction enzymes, rate of degradation of the genomes in different chromosomal regions, single nucleotide polymorphism, and unknown single-base pair mutations in the cancer genome that may change the pattern at a putative restriction site or the efficiency of PCR. Thus, complexity-reduction may in turn introduce an additional multiplicative noise while reducing the additive cross-hybridization noise. While all these introduce many challenges for arrayCGH based methods, they must be dealt with carefully and rigorously until alternative direct methods (such as methods based on single-molecule mapping and sequencing) replace arrays, and, consequently, reliance on PCR.

For arrayCGH technologies, optical and cross-hybridization noises are relatively better-understood parts of the microarray signals. Many other less-understood sources of noise exist. For example, as described earlier, few or no sources of noise adequately explain why a large proportion (30-40%) of MM probes exhibit a bigger response than their PM counterpart. Purely statistical modeling has proven insufficient to explain this lacuna. Examination of sequence-specific models may provide a better explanation, although initial efforts utilizing the dinucleotide models have so far proven inadequate.

One exemplary mathematical model of the data generated by these chips follows. Consider a genomic location L and two nucleotide sequences $s_{L,x}$ and $s_{L,y}$ starting at that location in the two copies of a diploid genomes. Further, consider the case when $s_{L,x}$ and $s_{L,y}$ differ, possibly in just one single nucleotide polymorphism; $c_x$ and $c_y$ are their respective copy numbers in the whole genome and all copies are selected in the reduced complexity representation. The gene chip in this example may contain four probes: $p_x$ in $s_{L,x}$; $p_y$ in $s_{L,y}$; $p_{x'}$, $p_{y'}$ not in G; and $p_x$ similar to $p_{x'}$ and $p_y$ similar to $p_{y'}$. Thus, after PCR amplification, some $K_x c_x$ amount of DNA may exist that is complementary to the probe $p_x$, K' may be approximately equal to $K'_x$ (roughly of the same values as $K'_y$, $K'_{x'}$, or $K'_{y'}$) amount of DNA that is additionally approximately complementary to the probe $p_x$. If the probe has an affinity $\phi_x$, then the measured intensity is can be expressed as $$[K_x c_x + K']\phi_x + \epsilon = [c_x + K'/K_x]\phi'_x + \epsilon,$$

where $\epsilon$ is an additive noise Gaussian noise, and $\phi'_x = K_x \phi_x$ is an amplified affinity. In particular, there may be four values of measured intensities:

$$I_x = [c_x + K'/K_x]\phi'_x + \epsilon$$

$$I_{x'} = [K'/K_x]\phi'_x + \epsilon$$

$$I_y = [c_y + K'/K_y]\phi'_y + \epsilon$$

$$I_{y'} = [K'/K_y]\phi'_y + \epsilon.$$

By comparing these values with a large number of experiments with normal or tumor genomes for which $c_x$ is already known to be 1 for a large fraction of the probes, the exemplary embodiment may estimate $\phi'_x$. On the other hand, if the affinity values are known (i.e., $\phi'_x$s), then the exemplary embodiment solve a linear regression to estimate $c_x$s, and further refine them to even better estimations (i.e., $c_x^*$s) using a "segmenter" methodology, which exploits the fact that same genomic copy-number changes will appear to be locally clustered over segments whose breakpoints are likely to follow a known distribution (e.g., uniform) and whose length will have a known distribution (e.g., exponential). Iteration over these two steps may result in better estimations of both affinity values and copy-number estimations.

Such concepts may be generalized to explain how the methodology may be generalized where a sequence of normal or tumor data are added one at a time while improving the affinity estimation (as well as copy-number estimation).

D. Statistical Estimation Method

The exemplary statistical estimation method may include several steps. The key steps are as follows: (1) Background Correction, (2) Normalization, (3) Copy-Number Estimation, and (4) Improved Estimator for Copy-Numbers.

The exemplary embodiment may focus on a probe j in some probe set. The probe j generally has an affinity parameter $\phi_j$. Assume that in a CGH experiment i, the following values are obtained: $U_{i,j}$ is the PM value and $W_{i,j}$ is the MM value. Assume that there have been n such experiments, and using some algorithm, the exemplary embodiment may compute the a signal value $I_{i,j}$. Thus, $I_{i,j}=c_{i,j}\phi_j+\epsilon$, where $c_{i,j}$ is the true-copy number. Also, the exemplary embodiment may next compute an estimate $C_{i,j}$ for the "copy-number" and even another estimator $C^*_{i,j}$, after segmentation. There is also a p-value $p^*_{i,j}$, associated with $C^*_{i,j}$, which can be translated to some weight function $w^*_{i,j}$, which takes a numerical value in the range [0,1] with 0 implying no confidence in the estimate and 1 implying complete confidence.

E. Background Correction

At the end of these n experiments, our estimate for $\phi_j=\Phi_{n,j}$. Following the earlier discussion, for purposes of the exemplary embodiment's operation it may be assumed that $I_{i,j}-C^*_{i,j}\Phi_{n,j}$ follows a normal distribution $N(\mu_n, \sigma_n)$. Similarly, the exemplary embodiment may employ a simplifying assumption that $W_{i,j}$ also follows the same normal distribution $N(\mu_n, \sigma_n)$.

Assuming that the data so far reveals a distribution for the U's (signals) to be describable as f(U). Then a generalized RMA may be derived to show how the I-values can be computed from U-values, for the interesting case of the distribution f being exponential with parameter $\alpha$, $$I' = U - \mu_n - \left[\alpha\sigma_n^2 - \frac{\varphi_{N(0,1)}(a'/b')}{\varphi_{N(0,1)}(a'/b')}\right]$$

$$\left\{\frac{1}{1+\beta'B_{\sigma_n}/\Phi_{N(0,1)}(a'/b')}\right\} + \left[\frac{b_{\sigma_n}}{B_{\sigma_n}}\right]\left\{\frac{1}{1+\Phi_{N(0,1)}(a'/b')/(\beta'B_{\sigma_n})}\right\}$$

where $$a' = U - \mu_n - \sigma_n^2\alpha$$

$$b' = \sigma_n$$

$$b_{\sigma_n} = \sum_{i=1}^{n}[I_{i,j} - U + \mu_n]\varphi_{N(0,1)}(I_{i,j} - U + \mu_n)$$

$$B_{\sigma_n} = \sum_{i=1}^{n}\varphi_{N(0,1)}(I_{i,j} - U + \mu_n)$$

and, as standard, $$\varphi_{N(0,\sigma)}(x) = \frac{1}{\sqrt{2\pi}\,\sigma}e^{-x^2/2\sigma^2},$$

$$\Phi_{N(0,\sigma)}(x) = \int_{-\infty}^{x}\phi_{N(0,\sigma)}(t)dt.$$

If $\beta=0$, then the above formula is a classical RMA correction with exponential prior, and, if $\beta\to\infty$, the above formula corrects using the empirical prior.

E. Normalization

The exemplary embodiment may further correct the I' values computed in the earlier step in order to determine new I values so that these values may follow a fixed distribution independent of any experiment. Thus, this normalization operation may correct for variability among experiments due to non-uniformity in sample preparation, complexity reduction, pCR amplification, and so forth. A model-based approach uses a parametric model with parameters optimized for each experiment, and involves a relatively complex implementation. One such implementation uses a QQ-normalization and is non-parametric, while avoiding bias introduced by assumptions implicit in the model. As an example, assume that all experiments seen so far (thus including the current experiment) are presented in sorted order and means of all the values for every fixed rank have been computed. A QQ-normalization operation for the current experiment may replace the current value at a fixed rank by the rank-mean and permute back these new values for the current experiment in order to recover a correct probe order. Thus, the normalized intensity value for a probe is "corrected" to the rank-mean value for the probe, virtually preserving the rank order among the probes while making the normalized intensity values have the same distribution across all the experiments. The exemplary embodiment may further employ these intensity values as explained herein.

F. Copy-Number Estimation

Thus, the exemplary embodiment may now solve the following system of nonlinear (but affine) regression equations:

$$I_{n+1,j} = C\phi_j + \varepsilon$$
$$I_{1,j} = C^*_{1,j}\phi_j + \varepsilon$$
$$I_{2,j} = C^*_{2,j}\phi_j + \varepsilon$$
$$\ldots$$
$$I_{n,j} = C^*_{n,j}\phi_j + \varepsilon$$

Note that all the probes in the same probe-set typically must have the same copy-number value C. Accordingly, C is the weighted-average of all the $(I_{n+1,j}/\phi_j)$'s from the probe-set with weights $\phi_j^2$. That is, $$C = \frac{\sum_{j\in probe\text{-}set} I_{n+1,j}\phi_j}{\sum_{j\in probe\text{-}set}\phi_j^2}.$$

The "corrected" affinity values themselves can also be computed by a linear-regression operation executed on the set of affine equations, shown earlier. Thus, $\phi_j$ is the weighted averages of all the $(I_{i,j}/c_{i,j})$'s with weights $c_{i,j}^2$. That is, $$\phi = \frac{CI_{n+1,j} + \sum_{i=1}^{n} w_{i,j}^* C_{i,j}^* I_{i,j}}{C^2 + \sum_{i=1}^{n} w_{i,j}^* C_{i,j}^{*2}} = \frac{CI_{n+1,j} + \lambda_{n,j}}{C^2 + \Lambda_n}.$$

Combining the two equations above, the exemplary embodiment may determine a quadratic equation for C, taking the following form:

$$C^2 B_n - C(\Lambda_n \Gamma_n - A_n) - \Lambda_n B_n = 0,$$

where $$A_n = \sum_{j \in probe\text{-}set} \lambda_{n,j}^2,$$

$$B_n = \sum_{j \in probe\text{-}set} I_{n+1,j} \lambda_{n,j},$$

$$\Gamma_n = \sum_{j \in probe\text{-}set} I_{n+1,j}^2.$$

Generally, the larger of the two real roots of the above equation gives the best estimator for C.

G. Improved Estimator for Copy-Numbers Using Segmenter

In a final operation, one exemplary embodiment may locally cluster the probes with similar copy number values into small number of contiguous segments and replace the estimated C-values by the segment average, C*-value. These values may be further normalized in order to provide correct allelic values. The corrected values are used in estimating the copy-number in the subsequent experiments.

Also, note that once the exemplary embodiment has the C*-values for the (n+1)th experiment, the exemplary embodiment may also update affinity estimations as follows:

$$\Phi_{n+1,j} = \frac{C_{n+1,j}^* I_{n+1,j} + \lambda_{n,j}}{C_{n+1,j}^{*2} + \Lambda_n}.$$

The segmenter methodology employed by certain embodiments also returns a p-value for each segment, each probe-set and each probe. Those may be used for computing the weights $w_{n+1,j}^*$.

With these operations, the exemplary embodiment may compute the estimated copy numbers in the next subsequent experiment.

H. Example: Affy 10K Chip

Publicly available data from Affymetrix may be used to validate an exemplary embodiment. A data set for validation may contain 121 Affymetrix CEL files generated using the Affymetrix Mapping 10K 2.0 Array, consisting of readings from African American, Asian and Caucasian populations. The Mapping 10K 2.0 array generally allows efficient genotyping of over 10,000 Single Nucleotide Polymorphisms (SNPs) in a single array. Most of the SNPs on the chip are from the SNP Consortium (TSC) database and lie within one of 250 to 1000 base fragments that are amplified by the mapping assay.

This data may be preprocessed to remove nominal levels of background noise. The distributions of the individual data sets may be normalized. Neither of these steps is necessary for the exemplary embodiment described in this disclosure to work and no particular methodology for background noise removal and normalization are preferred.

Figure 6:
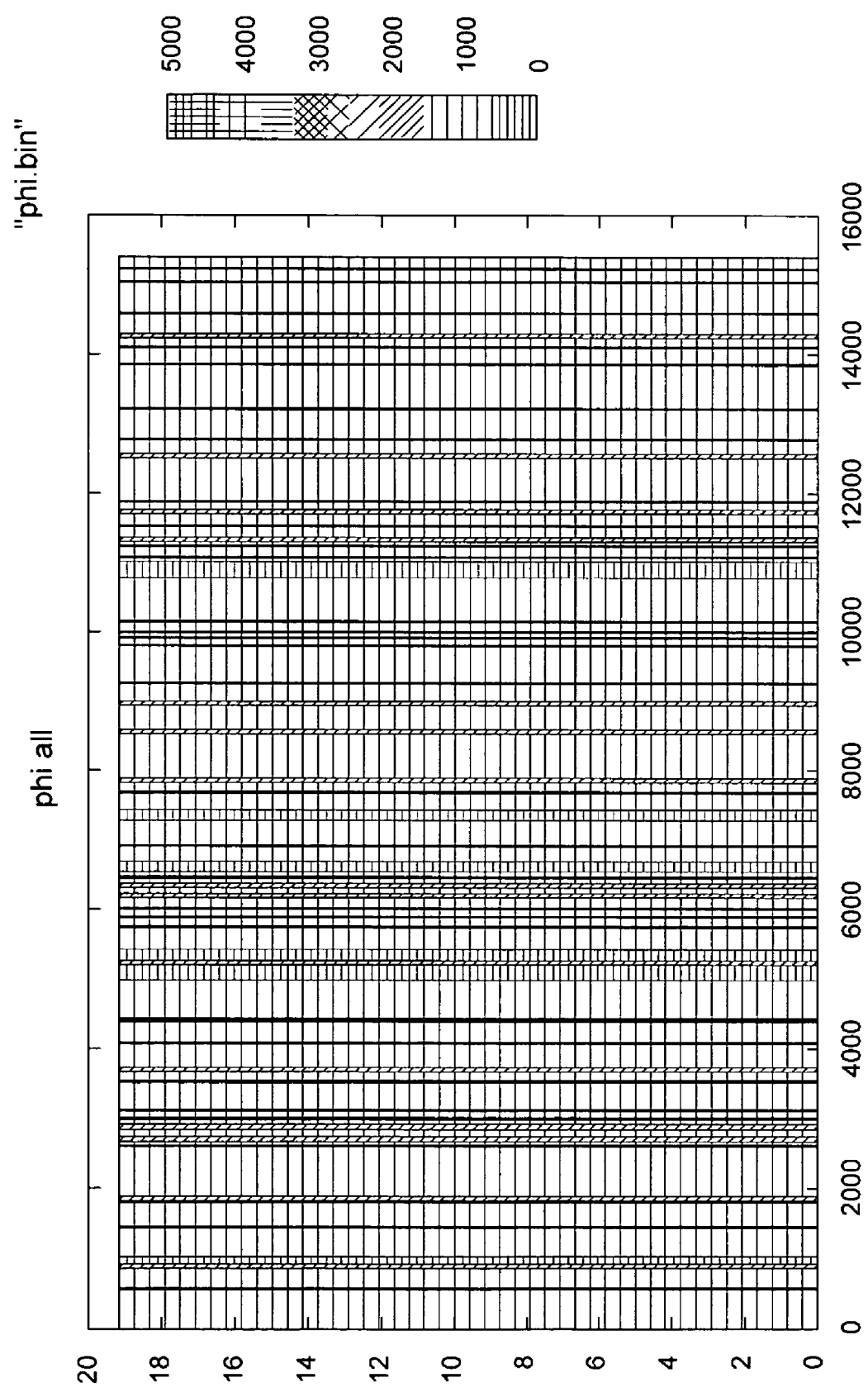
FIG. 6 shows a Phi-value estimation improving over 40 iterations.
Figure 7:
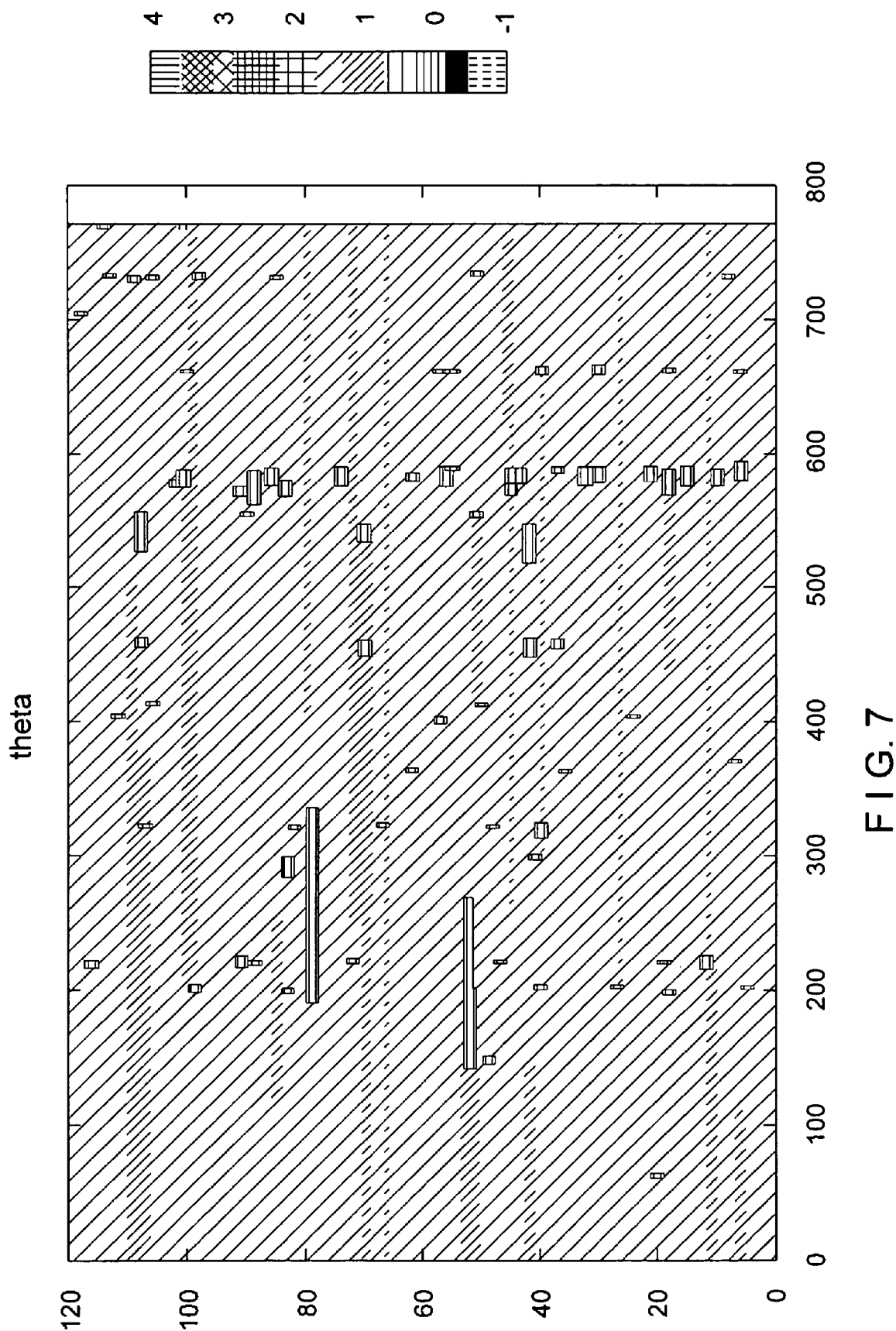
FIG. 7 shows C-values computed from sample Affymetrix 10K data set with 121 samples

For validation, the preprocessed data sets may be processed using the exemplary embodiment and the probe affinities may be calculated. The process typically requires only a few iterations (typically less than 30) of an EM algorithm to iteratively determine and improve an estimate for the probe affinities and the improved estimator for copy number described above. Once the probe affinities have been computed using a suitable set of training data, new data may be analyzed and the copy number determined without re-running the EM algorithm. FIG. 6 shows a phi-value estimation improving over 40 iterations, while FIG. 7 depicts C-values computed from sample Affymetrix 10K data set with 121 samples.

III. Third Exemplary Embodiment of the Invention

A. Introduction

Microarray-based comparative genomic hybridization (array-CGH) approach may provide rapid genome-wide assays and indicate copy-number variations of chromosomal segments in a tumor genome. For instance, chromosomal segments, deleted in a single or both copies of the diploid genomes of a group of cancer patients, may point to a location of tumor suppressor genes implicated in a cancer. A multipoint statistical method, presented here, may be capable of estimating the location of tumor suppressor genes by analyzing array-CGH data characterizing segmental deletions (hemi- or homo-zygous) in cancer genomes. One exemplary method may compute a multipoint score for intervals of consecutive probes and may also identify smaller sets of predictive probes that can then be used as biomarkers. The method may be applied to different simulated datasets as well as a real dataset. Generalization of the exemplary embodiment to detection of oncogenes and other disease genes may include a suitable modification to the underlying statistical model.

B. Overview

The process of carcinogenesis imparts many genetic changes to a cancer genome at many different scales: point mutations, translocations, segmental duplications and deletions. While most of these changes have no direct impact on the cellular functions, and may not contribute to the carcinogenesis in any obvious manner, few of these chromosomal aberrations have disproportionately significant impact on the cell's ability to initiate and maintain processes involved in tumor growth: ability to proliferate, escape senescence, achieve immortality, and signal to neighboring cells. Two classes of genes are critically involved in cancer development and are discernible in terms of their copy number variations: oncogenes that are activated or altered in function and tumor suppressor genes that are deactivated in cancer cells. Thus, the effect of oncogenes is via gain-of-function mutations that lead to malignancy. One type of mutation is amplification that increases the genomic copy number leading to over-expression of the oncogene product. The mutation is dominant, i.e. only a mutated allele is necessary for the cell to become malignant. Tumor-suppressor genes (TSGs) affect the cells via mutations that contribute to malignancy by loss of function of both alleles of the gene. A "two-hit" hypothesis for tumorigenesis has been widely recognized as a useful model in many cancers.

Whole-genomic data and related computational analysis may now lead to rapid discovery and characterization of important genetic changes, which in turn may present a systems-level understanding of the roles of oncogenes and tumor suppressor genes in cancer development at the molecular level. As an example, while BRCA1 and -2 tumor suppressor genes (TSGs) provide better understanding of familial breast cancer, and other tumor suppressor genes (TSGs), including PTEN and p53, do so for sporadic breast cancer, many tumor-suppressor genes may remain undiscovered and will yield easily to whole-genome analysis.

In many known approaches to a whole-genome analysis setup, microarray techniques have been used successfully to measure differences in a copy number of particular genomic regions between two different DNA samples. For example, array CGH can map copy number changes at practically any sequence of chromosomal locations in the genome, and from them extrapolate to infer segments of genome that have undergone the same degree of amplifications or deletions.

In order to explain this array-based technology, imagine that one can sample the genome uniformly (independently and identically distributed, or "i.i.d".) and reproducibly to create a large number of oligonucleotides (on the order of 100,000 probes) located every 30 kb or so. These selected oligonucleotides may be further assumed to be almost always from regions of the genome that do not share homologous sequences elsewhere in the genome, but have similar thermodynamic and hybridization properties. These oligonucelotide sequences (typically less than a few hundred base pairs long) occupy unique positions in the normal genome and typically have exactly two copies. If one such oligonucleotide belongs to a region in a cancer genome that has an altered copy number, say, c ($0 \leq c \neq 2$), then when the cancer genome is sampled, this oligonucleotide will occur with a probability that is c/2 times that of occurring in the regular genome. The copy number can be computed by a ratiometric measurement of the abundance of an oligonucleotide in a cancer sample measured against that in the regular genome. Such a technique may be generalized to measure the copy number variations for many probes simultaneously with high-throughput microarray experiments. Its signal-to-noise ratio may be further improved by reducing the complexity of the genome, employing multiple probe sets per location, employing probes with perfect-match and mismatch compositions, and through sets of calibrating experiments leading to probe characterizations.

In one embodiment of the invention, copy number changes may be used for tumor suppressor gene (TSG) identification. For example, suppose one has whole-genome analysis data for several patients suffering from the same specific class of cancer, putatively caused by loss-of-function in both alleles of the same tumor suppressor gene (TSG). In that case, the loss-of-function event may have many underlying causes, such as a non-synonymous point mutation in the exon, or a mutation in the regulatory region, small insertion-deletion event in the coding region, or a relatively large segmental deletion event that affects one or many exons of the gene. In each case the phenotypic result will be similar. However, whole-genome analysis will only identify segmental deletion events, exhibiting itself as smaller copy number for a genomic interval that overlaps with the genomic interval representing the tumor suppressor gene (TSG). Even though events representing small undetectable mutations will go unnoticed, by accounting for the copy number variations, one can infer the location of the tumor suppressor gene (TSG) implicated in the disease. The exemplary embodiment may evaluate every possible genomic interval and assign a score measuring how likely it is for that genomic interval to be a tumor suppressor gene.

C. Exemplary Methods

Details of one exemplary method for identification of tumor suppressor genes using a multipoint score function and now provided.

i. Definition of Relative Risk:

Given an interval I (i.e., a set of consecutive probes along the genome), the following formula may be used to compute the relative risk (RR) of disease in patients whose genomes contain a segment of the interval I deleted, as compared to the risk in patients whose genomes have no such segment from I deleted.

$$RR_{I,deleted} = \ln \frac{P(\text{disease} \mid I = \text{deleted})}{P(\text{disease} \mid I \neq \text{deleted})}$$

$$= \ln \left( \frac{P(I = \text{deleted} \mid \text{disease})}{P(I \neq \text{deleted} \mid \text{disease})} \times \frac{P(I \neq \text{deleted})}{P(I = \text{deleted})} \right)$$

The first factor in the product above can be estimated from the tumor samples available:

$$\frac{P(I \neq \text{deleted})}{P(I = \text{deleted})} = \frac{n_{I \neq deleted}}{n_{I = deleted}}$$

where $n_{I=deleted}$ is the number of tumor samples in which I is deleted, and $n_{I \neq deleted}$ is the number of tumor samples in which I is not deleted.

A second factor incorporates prior information. In order to compute this second factor, a probabilistic process assumed to model how data is generated. In a parsimonious model, the exemplary embodiment may assume that at each marker breakpoints occur as a Poisson process at a rate $\mu \geq 0$. At each of these breakpoints, there is a deletion with length distributed as an exponential random variable with parameter $\lambda \geq 0$.

Assuming the generative process described above, the probability that an interval I=[a,b] is deleted can be expressed as follows:

$$P([a, b] = \text{deleted}) = 1 - e^{-\mu(b-a)} e^{-(\mu/2\lambda)(1-e^{-\lambda a})} e^{-(\mu/2\lambda)(1-e^{-\lambda(G-b)})}$$

where [0,G] represents the region of interest (in one embodiment, the whole genome).

Using these equations, the exemplary embodiment may compute the "relative risk score" for an interval I. Generally speaking, high-scoring intervals are candidates for tumor suppressor genes (TSGs).

ii. Estimating Location of TSG

Since the exemplary embodiment may now use the score defined above to compute a likely location (or, in some embodiments, a set of most likely locations) for the tumor suppressor genes, the exemplary embodiment may now consider many focal points across the region of interest. More formally, to each focal point $x \in [0,G]$, the exemplary embodiment may associate a score as follows. Let $I_x$ be the set of all intervals (with length bounded by some specified upper bound) that contain x. Then $$S_x = \sum_{I \in I_x} RR_{I=deleted}$$

This score represents a measure of confidence that the focal point x belongs to an interval representing a disease-causing tumor suppressor gene.

Similarly, the embodiment may also associate two additional scores, $SL_x$ and $SR_x$, with a focal point. The former, denoted by $SL_x$, is the confidence that the point is the left margin of a tumor suppressor gene (TSG) and the latter, $SR_x$, is the confidence that the point is the right margin of a tumor suppressor gene (TSG). These scores are defined as follows. Let $\delta>0$ be a small positive number. The embodiment may define:

$$SL_x = \sum_{I \in IL_x} RR_{I=deleted}$$

where $IL_x$ is the set of intervals with the left margin in $[x-\delta, x]$. Similarly, $$SR_x = \sum_{I \in IR_x} RR_{I=deleted}$$

where $IR_x$ is the set of intervals with the right margin in $[x, x+\delta]$. These two scores generally provide an estimation of the true position of the TSG.

iii. Significance Testing

The exemplary embodiment may also attach a statistical significance to the regions discovered using the method described above. The exemplary embodiment may also use results from the theory of scan statistics. For each individual in a sample, the embodiment may estimate the number of breakpoints and their positions using a segmentation methodology discussed below. From the inferred breakpoints in each individual, the embodiment obtain an overall total of $N$ breakpoints distributed along the chromosome. Under the null hypothesis (i.e., "no tumor suppressor gene resides on the chromosome"), these points may be treated by the exemplary embodiment as uniformly distributed along the chromosome. However, if there is an unusual cluster of breakpoints in a small region, this may indicate the presence of a tumor suppressor gene in the region.

Let $S_w$ be the largest number of breakpoints in any interval of length w. This statistic is called the scan statistic, and using the distribution of the statistic $S_w$, the embodiment may determine where the null hypothesis is violated. In particular, the embodiment may find the tail probability: $P(S_w \geq k)$. As known to those skilled in the art, an approximation for $P(S_w \geq k)$ exists, using the following notations. Let $$b(k; N, w) = \binom{N}{k} w^k (1-w)^{N-k},$$

$$G_b(k; N, w) = \sum_{i=k}^{N} b(i; N, w).$$

Then $$P(S_w \geq k) \approx (kw^{-1} - N - 1)b(k; N, w) + 2G_b(k; N, w),$$

which is accurate when $P(S_w \geq k) < 0.1$.

Since w cannot be fixed in advance, the exemplary embodiment typically employs several values. For instance, the exemplary embodiment may compute the scan statistic for several lengths w, starting with the average distance between markers and increasing the length such that, at its maximum, it is the average length plus twice the standard deviation of a gene. In order to correct for the estimation obtained by sampling over different values of w, the embodiment may use a Bonferroni inequality based on the 1 possible window sizes. In this scheme, to ensure an overall significance level $\alpha$, the embodiment may divide by $1$, the number of window sizes.

iv. Estimating Parameters

The defined score is based on the parameters $\lambda$ and $\theta$ ($\lambda$ is the mean length of deletion and $\theta$ is the mean number of breakpoints). The embodiment may estimate these parameters using a statistical method for detecting genomic copy-number variations from array CGH data. The exemplary embodiment segments the contiguous probes of similar copy-number values, thus describing the genomes in terms of alternating segments of normal and abnormal regions, and may also classify abnormal regions in terms of duplicated and deleted segments potentially harboring oncogenes and tumor-suppressor genes, respectively. From the inferred segmentation, the embodiment may estimate the average number of breakpoints and also the average length of a deletion.

Furthermore, the exemplary embodiment may employ the segmentation of individual samples to obtain the positions of the breakpoints in each sample, which is necessary to compute the scan statistic in the preceding section.

D. Results

An exemplary embodiment has been applied to simulated data as well as real data.

i. Simulated Data

Simulations were performed under various scenarios. The simulations used S=50 or S=100 tumor samples. Each sample constitutes a microdissection of N=100 diseased cells. The length of the chromosome in the various simulations is 100 Mb and the number of probes is 20,000, resulting in a density of 1 probe every 5 kb. The exemplary embodiment may assume a Poisson process that generates breakpoints along the genome. The mean number of breakpoints is $2$. At each breakpoint a deletion is generated with mean length 20,000. The position of the TSG is specified; the embodiment may assume the TSG has fixed length, namely 20 kb. During this process a cell may incur a deletion overlapping the TSG, in which case it will start multiplying itself and generate many copies (for example, 100 copies) of itself. In order to generate noisy copies of the original diseased cell, these copies were left to evolve independently until the exemplary embodiment would collect the information.

Operation of the exemplary embodiment was verified under many different simulated scenarios. Each scenario shares the characteristics outlined above. However, they differ in the composition of the sample: a certain fraction ($p_{SPORADIC}$) is sporadic, a certain fraction ($p_{HOMO}$) have homozygous deletion of the TSG and the rest ($p_{HEMI}$) have hemizygous deletion of the TSG. For each scenario, both S=50 and S=100 are simulated. In these cases, exemplary embodiment detected the TSG with relatively accurate boundaries. The exemplary embodiment was also applied to real datasets (e.g., on breast cancer) with comparable results.

IV. Conclusion

The foregoing merely illustrates the principles of the invention. Various modifications and alterations to the described embodiments will be apparent to those skilled in the art in view of the teachings herein. It will thus be appreciated that those skilled in the art will be able to devise numerous systems and methods and software arrangements that, although not explicitly shown or described herein, embody the principles of the invention and are thus within the spirit and scope of the invention.

The contents of all publications and references cited herein are hereby incorporated herein by reference in their entireties.

What is claimed is:

1. A storage medium storing a software program that is adapted for detecting at least one variation in a numerical data ordered sequentially from data contained in at least one dataset, wherein the software program, when executed by a processing arrangement, is configured to cause the processing arrangement to execute the operations comprising:
   a) receiving the at least one dataset which includes sequential data;
   b) receiving prior information of statistical character associated with the at least one dataset in a form of models of probability distributions;
   c) partitioning the sequential data into non-overlapping intervals; and
   d) providing an indication of the at least one variation in the numerically ordered data based on further information associated with at least one of each of the intervals.

2. The storage medium of claim 1, wherein the sequentially ordered numerical data contained in at least one dataset consists of at least one of (i) vectors of identical dimensions, (ii) numbers, or (iii) sequences of numbers of identical length.

3. The storage medium of claim 1, wherein the software program is further configured to cause the processing arrangement to obtain the sequential data by analyzing biological markers.

4. The storage medium of claim 3, wherein the sequential data is obtained using at least one of (i) micro-arrays, or (ii) techniques which manipulate single molecules at a time.

5. The storage medium of claim 1, wherein the prior information contains states, state transitions, probability distributions over states, and conditional probability distributions over possible state transitions for all given current states.

6. The storage medium of claim 5, wherein the sequential data includes at least one of (i) vectors of identical dimensions, (ii) numbers, (iii) sequences of numbers of identical length, or (iv) biologically relevant local parameters.

7. The storage medium of claim 5, wherein the states of the prior information contain loss of heterozygosity ("LOH") information.

8. The storage medium of claim 5, wherein the states of the prior information consist of at least one of:
   I. a regular state, or
   II. a deviated state.

9. The storage medium of claim 5, wherein the states of the prior information are included in each of the intervals.

10. The storage medium of claim 1, wherein the software program is further configured to cause the processing arrangement to examine a quality of at least one result obtained in steps (c)-(e).

11. The storage medium of claim 10, wherein the result is evaluated according to the following criteria:
   I. a goodness of fit which determines a quality of estimated parameters in each of the intervals plausibly generating the data therein, and
   II. a prevention from overfitting such that successive non-overlapping intervals have substantially-separated parameter values.

12. The storage medium of claim 11, wherein the appropriateness of fit in each of the intervals is obtained by taking at least one of (i) an average squared deviation of data samples in the respective interval, (ii) a square root of the average squared deviation of the data samples in the respective interval, or (iii) an average absolute deviation of data samples in the respective interval.

13. A storage medium storing a software program adapted for detecting variations in genome copy number in one or more genetic samples from data contained in at least one dataset, wherein the software program, when executed by a processing arrangement, is configured to cause the processing arrangement to execute the operations comprising:
   a) receiving the at least one dataset; and
   b) partitioning the genomes of the one or more genetic samples into non-overlapping intervals from the at least one dataset;
   wherein the non-overlapping intervals are indicative of at least one variation in the genome copy number in the one or more genetic samples, and wherein the partitioning of the genomes of the one or more genetic samples is performed by selecting an interval structure for the at least one dataset that maximizes a likelihood function.

14. The storage medium of claim 13, wherein the data contained in the at least one dataset is obtained by analyzing the genetic samples with a plurality of genetic probes.

15. The storage medium of claim 13, wherein the likelihood function is provided as $$L(\langle i_1, \mu_1, i_2, \mu_2, \ldots, i_k, \mu_k \rangle) =$$

$$e^{-p_b N} \frac{(p_b N)^k}{k!} \frac{1}{(2\pi\sigma^2)^{\frac{n}{2}}} \cdot \prod_{i=1}^{n} e^{-\frac{(x_i - \mu_j)^2}{(2\sigma^2)}} \cdot p_e^{\#global} (1 - p_e)^{\#local},$$

where #global is a number of "normal" probes with the global mean, #local is a number of remaining probes, $p_r$ is a probability that a particular probe is normally distributed, $p_b N$ is a Poisson parameter, $\mu$ is the estimated sample mean for the interval, and $\sigma$ is the standard deviation of the sample.

16. The storage medium of claim 13, wherein the partitioning is performed by selecting an interval structure for the at least one dataset that minimizes a negative log likelihood of a likelihood function.

17. The storage medium of claim 16, wherein the negative log likelihood is provided as $$-\log L(I') = -\log L(I) + \frac{1}{2\sigma^2} \sum_{j=i_k+1}^{i_{k+1}} (x_j - \mu_{k+1})^2 - \log(p_b N) +$$

$$\log(k+1) + \frac{i_{k+1} - i_k}{2} \log(2\pi\sigma^2) - (i_{k+1} - i_k) \begin{cases} \log p_e \\ \log(1 - p_e) \end{cases}$$

wherein $i_k+1$ to $i_{k+1}$ is included only if the added interval extending from $i_k+1$ to $i_{k+1}$ is global.

18. The storage medium of claim 16, wherein the selection of an interval structure is performed by computing an optimality property satisfied by the negative log likelihood function according to the formula $$Opt_n = \operatorname*{arg\,min}_{I \in \text{Working Set}_n} (-\log L(I)),$$

wherein $$\text{Working Set}_n = \bigcup_{i<n} \{Opt_i \circ (n, \mu_e), Opt_i \circ (n, \text{mean}(x_{i+1}, \ldots, x_n))\}.$$

19. A storage medium storing a software program that is adapted for detecting at least one variation in genome copy number in one or more genetic samples from data contained in at least one dataset, wherein the software program, when executed by a processing arrangement, is configured to cause the processing arrangement to execute the operations comprising:
 a) receiving the at least one dataset; and
 b) partitioning the genomes of the one or more genetic samples into non-overlapping intervals from the at least one dataset;
 wherein the non-overlapping intervals are indicative of the at least one variation in the genome copy number in the one or more genetic samples, and wherein the partitioning of the genomes of the one or more genetic samples is performed by selecting an interval structure for the at least one dataset that maximizes a likelihood function.

20. The storage medium of claim 1, wherein, when the software program is executed by the processing arrangement, the software program is further configured to cause the processing arrangement to output information associated with the at least one variation in the numerically ordered data (i) in at least one of a computer accessible format or a computer readable format or (ii) on an output device.

21. The storage medium of claim 13, wherein, when the software program is executed by the processing arrangement, the software program is further configured to cause the processing arrangement to output information associated with the at least one variation in the genome copy number in the one or more genetic samples (i) in at least one of a computer accessible format or a computer readable format or (ii) on an output device.

22. The storage medium of claim 19, wherein, when the software program is executed by the processing arrangement, the software program is further configured to cause the processing arrangement to output information associated with the at least one variation in the genome copy number in the one or more genetic samples (i) in at least one of a computer accessible format or a computer readable format or (ii) on an output device.

23. The storage medium of claim 19, wherein the data contained in the at least one dataset is obtained by analyzing the genetic samples with a plurality of genetic probes.

24. The storage medium of claim 19, wherein the likelihood function is provided as $$L(\langle i_1, \mu_1, i_2, \mu_2, \ldots, i_k, \mu_k \rangle) = e^{-p_b N} \frac{(p_b N)^k}{k!} \cdot \frac{1}{(2\pi\sigma^2)^{\frac{n}{2}}} \cdot \prod_{i=1}^{n} e^{-\frac{(x_i - \mu_j)^2}{(2\sigma^2)}} \cdot p_e^{\#global} (1 - p_e)^{\#local},$$

where #global is a number of "normal" probes with the global mean, #local is a number of remaining probes, $p_r$ is a probability that a particular probe is normally distributed, $p_b N$ is a Poisson parameter, $\mu$ is the estimated sample mean for the interval, and $\sigma$ is the standard deviation of the sample.

25. The storage medium of claim 1, wherein the further information comprises information associated with an interval structure.

26. A process for detecting at least one variation in a numerical data ordered sequentially from data contained in at least one dataset, comprising:
 a) receiving the at least one dataset which includes sequential data;
 b) receiving prior information of statistical character associated with the at least one dataset in a form of models of probability distributions;
 c) using a hardware processing arrangement, partitioning the sequential data into non-overlapping intervals; and
 d) providing an indication of the at least one variation in the numerically ordered data based on further information associated with at least one of each of the intervals.

27. The process of claim 26, wherein the sequentially ordered numerical data contained in at least one dataset consists of at least one of (i) vectors of identical dimensions, (ii) numbers or (iii) sequences of numbers of identical length.

28. The process of claim 26, further comprising obtaining the sequential data by analyzing biological markers.

29. The process of claim 28, wherein the sequential data is obtained using at least one of (i) micro-arrays or (ii) techniques which manipulate single molecules at a time.

30. The process of claim 26, wherein the prior information contains states, state transitions, probability distributions over states, and conditional probability distributions over possible state transitions for all given current states.

31. The process of claim 30, wherein the sequential data includes at least one of (i) vectors of identical dimensions, (ii) numbers, (iii) sequences of numbers of identical length or (iv) biologically relevant local parameters.

32. The process of claim 30, wherein the states of the prior information contain loss of heterozygosity ("LOH") information.

33. The process of claim 30, wherein the states of the prior information consist of at least one of:
 I. a regular state, or
 II. a deviated state.

34. The process of claim 30, wherein the states of the prior information are included in each of the intervals.

35. The process of claim 26, further comprising examining a quality of at least one result obtained in procedures (c)-(e).

36. The process of claim 35, wherein the result is evaluated according to the following criteria:
 I. a goodness of fit which determines a quality of estimated parameters in each of the intervals plausibly generating the data therein, and
 II. a prevention from overfitting such that successive non-overlapping intervals have substantially-separated parameter values.

37. The process of claim 36, wherein the appropriateness of fit in each of the intervals is obtained by taking at least one of (i) an average squared deviation of data samples in the respective interval, (ii) a square root of the average squared deviation of the data samples in the respective interval or (iii) an average absolute deviation of data samples in the respective interval.

38. The process of claim 26, further comprising outputting information associated with the at least one variation in the numerically ordered data (i) in at least one of a computer accessible format or a computer readable format or (ii) on an output device.

39. The process of claim 26, wherein the further information comprises information associated with an interval structure.

40. A process for detecting at least one variation in genome copy number in one or more genetic samples from data contained in at least one dataset, comprising:
  a) receiving the at least one dataset; and
  b) using a hardware processing arrangement, partitioning the genomes of the one or more genetic samples into non-overlapping intervals from the at least one dataset;
  wherein the non-overlapping intervals are indicative of the at least one variation in the genome copy number in the one or more genetic samples, and wherein the partitioning of the genomes of the one or more genetic samples is performed by selecting an interval structure for the at least one dataset that maximizes a likelihood function.

41. The process of claim 40, further comprising outputting information associated with the at least one variation in the genome copy number in the one or more genetic samples (i) in at least one of a computer accessible format or a computer readable format or (ii) on an output device.

42. The process of claim 40, wherein the data contained in the at least one dataset is obtained by analyzing the genetic samples with a plurality of genetic probes.

43. The process of claim 40, wherein the likelihood function is provided as $$L(\langle i_1, \mu_1, i_2, \mu_2, \ldots, i_k, \mu_k \rangle) = e^{-p_b N} \frac{(p_b N)^k}{k!} \frac{1}{(2\pi\sigma^2)^{\frac{n}{2}}} \cdot \prod_{i=1}^{n} e^{-\frac{(x_i - \mu_j)^2}{(2\sigma^2)}} \cdot p_e^{\#global}(1 - p_e)^{\#local},$$

where #global is a number of "normal" probes with the global mean, #local is a number of remaining probes, $p_r$ is a probability that a particular probe is normally distributed, $p_b N$ is a Poisson parameter, $\mu$ is the estimated sample mean for the interval, and $\sigma$ is the standard deviation of the sample.

* * * * *